United States Patent
Fiorda et al.

(10) Patent No.: US 9,561,531 B2
(45) Date of Patent: *Feb. 7, 2017

(54) COMPOSITION AND METHOD FOR HYDROCARBON AND LIPID DEGRADATION AND DISPERSAL

(71) Applicant: GREEN ON INDUSTRIES, INC., Maple (CA)

(72) Inventors: Antonio Fiorda, Maple (CA); Terrence J McGuire, Brampton (CA)

(73) Assignee: Green On Industries Inc., Toronto (CA)

( * ) Notice: Subject to any disclaimer, the term of this patent is extended or adjusted under 35 U.S.C. 154(b) by 2 days.

This patent is subject to a terminal disclaimer.

(21) Appl. No.: 14/624,279

(22) Filed: Feb. 17, 2015

(65) Prior Publication Data
US 2015/0158065 A1    Jun. 11, 2015

Related U.S. Application Data

(63) Continuation-in-part of application No. 14/158,099, filed on Jan. 17, 2014, now Pat. No. 9,175,247, which is a continuation of application No. 13/790,879, filed on Mar. 8, 2013, now abandoned, which is a continuation of application No. 13/495,236, filed on Jun. 13, 2012, now Pat. No. 8,415,286.

(60) Provisional application No. 61/940,910, filed on Feb. 18, 2014.

(51) Int. Cl.
| | |
|---|---|
| *B09C 1/10* | (2006.01) |
| *C02F 3/34* | (2006.01) |
| *C12N 1/20* | (2006.01) |
| *C12N 1/14* | (2006.01) |
| *A62D 3/02* | (2007.01) |
| *C02F 1/68* | (2006.01) |
| C02F 101/32 | (2006.01) |
| E02B 15/04 | (2006.01) |

(52) U.S. Cl.
CPC . *B09C 1/10* (2013.01); *A62D 3/02* (2013.01); *B09C 1/105* (2013.01); *C02F 1/682* (2013.01); *C02F 3/343* (2013.01); *C12N 1/14* (2013.01); *C12N 1/20* (2013.01); *C02F 2101/32* (2013.01); *C02F 2305/04* (2013.01); *E02B 15/041* (2013.01)

(58) Field of Classification Search
None
See application file for complete search history.

(56) References Cited

PUBLICATIONS

Das et al., Crude petroleum-oil biodegradation efficiency of *Bacillus subtilis* and *Pseudomonas aeruginosa* strains isolated from a petroleum-oil contaminated soil from North-East India, Bioresource Technology 98 (2007) 1339-1345.*

* cited by examiner

*Primary Examiner* — Suzanne M Noakes
*Assistant Examiner* — Stephen Chong
(74) *Attorney, Agent, or Firm* — Matthew D. Powell; Gilbert's LLP (57) ABSTRACT

The present invention is directed toward a bioremediation product, its method of manufacture and method of use. A blend of microorganisms, cleansers and surfactants is disclosed which is non-toxic and solvent free, and which has the ability to accelerate the breaking down process of oils, materials such as benzene, toluene, and xylene (BTEX); petroleum hydrocarbon fractions F1-F4 (as defined by CCME2000), polycyclic aromatic hydrocarbons (PAH), paraffin waxes, volatile organics, molds, and the like; while simultaneously providing a biological component which is effective to reduce the total petroleum hydrocarbon levels to zero at an accelerated rate. The product is useful for bioremediation and as an oil dispersant composition useful in treating oil spills, and for cleanup of the shoreline, animals, plants, and equipment.

6 Claims, 3 Drawing Sheets

COMPOSITION AND METHOD FOR HYDROCARBON AND LIPID DEGRADATION AND DISPERSAL

CROSS-REFERENCE TO RELATED APPLICATIONS

This application is a continuation-in-part of U.S. application Ser. No. 14/158,099, filed on Jan. 17, 2014, now U.S. Pat. No. 9,175,247, which issued on Nov. 3, 2015; which is a continuation of U.S. application Ser. No. 13/790,879, filed on Mar. 8, 2013, and now abandoned; which is a continuation of U.S. application Ser. No. 13/495,236, filed on Jun. 13, 2012, now U.S. Pat. No. 8,415,286, which issued on Apr. 9, 2013; the contents of each are incorporated by reference herein in their entirety.

FIELD OF THE INVENTION

This invention relates to a solvent free, non-toxic composition useful for hydrocarbon and lipid dispersal and degradation and methods for their production and use.

BACKGROUND OF THE INVENTION

The oil industry's preferred method of marine spill response in the United States is the use of chemical dispersants. The use of such dispersants serves a useful purpose since it does cause the oil to sink out of sight, eliminating the severity of surface associated phenomenon such as oil soaked birds and the like. Unfortunately, many of the dispersants listed in the EPA National Contingency Plan's Product Schedule have inherent toxicity issues, which often times exacerbate the problem. As a result of their application, the oil/dispersant mixture is brought to much lower depths, where the presence of this toxic blend causes a variety of problems over time.

The problem with dispersants is illustrated by what has been occurring in the Gulf of Mexico subsequent to the BP oil spill. The testing authorities often use outdated and minimal testing procedures for dispersants, which results in an underestimation of the chemicals' impacts to marine and human life. Many of the reported chemicals in dispersants are known human health hazards; as are many of the proprietary chemicals incorporated therein. Dispersants have been linked, or heavily implicated, with the widespread occurrences of lesions and maladies in fish and shellfish, dolphin deaths, and dramatic decline in populations of some Gulf species such as shrimp and killifish.

As a result of past catastrophic events such as the Exxon Valdez spill in Alaska, and the recent oil spills that occurred in the Gulf of Mexico, we have all become aware of the dire need to properly address the situation without further damaging the environment and destroying animal and sea life.

This long felt need for a non-toxic, solvent free dispersant has been provided by the instant inventors as disclosed in related U.S. Pat. No. 8,415,286, which issued on Apr. 9, 2013. The unique dispersant product of the '286 patent, designated DXR-02™ has been shown to efficiently breaks down grease, grime and crude oil at the molecular level, by breaking down the hydrocarbon chains and preventing the oil molecules from ever reforming again.

Once DXR-02™ comes in contact with the oil, any agitation (such as motion of the waves and currents in the ocean) will accelerate the breaking down process of the oil, leaving DXR-02™ to biodegrade within 9 to 12 days. After this process is completed, the dispersed oil will be naturally absorbed back into the environment, without any further damage or danger to nature.

In order to provide an improved product having superior capabilities for degrading both hydrocarbons and lipids, the instant inventors have determined strains of microorganisms which are compatible with the DXR-02™, and have the ability to enhance the action of the surfactant, for example in soil remediation, by providing a microbial degradation function for hydrocarbons, lipids, and combinations thereof.

DXR-02™ is a clear, slightly yellow liquid that is formed from a proprietary blend of cleansers and surfactants and a high dilution of pure water. The unique blend of ingredients exhibit the ability to break down the hydrocarbon chain and prevent any reconnection, thereby resulting in a unique oil dispersant utility. The pH of about 8.5 renders it non-alkaline, which in turn makes it good for the environment. Water being the catalyst, the more water you use the better it works. DXR-02™ represents a 50% dilution of DXR™, which is the concentrate. Depending upon the application, a choice can be made as to use of the diluted or more concentrated product. For mixtures with microbes for soil remediation and the like, DXR™ is generally used.

DESCRIPTION OF THE PRIOR ART

U.S. Pat. No. 7,915,212, to Yeung et al., relates to a block polymeric material. Typically the block polymer comprises units capable of having an average cationic charge density of about 15 or less, preferably 5 or less, more preferably from about 0.05 to about 5, even more preferably from about 0.05 to about 2.77, even more preferably from about 0.1 to about 2.75, most preferably from about 0.75 to about 2.25 units per 100 daltons molecular weight at a pH of from about 4 to about 12. The polymeric material is a suds enhancer and a suds volume extender for personal care products such as soaps and shampoos. The compositions have increased effectiveness for preventing re-deposition of grease during hand and body washing. The polymers are also effective as a soil release agent in fabric cleaning compositions. The polymeric material is also effective in oil well treating foam, fire-fighting foam, hard surface cleaning foam, shaving cream, post-foaming shaving gel depilatories and as a coagulant/retention aid for titanium dioxide in paper making.

U.S. Pat. No. 6,261,463, to Jacob et al., is directed toward an effective and non-toxic oil spill dispersant which includes a predominately oil-soluble surfactant (e.g., polyethylene glycol mono-oleate) with a predominately water-soluble surfactant (e.g., cocoamide) and a co-solvent for coupling a mixture of the predominately oil-soluble surfactant and the oil spill, with the predominately water-soluble surfactant. Water is included in the combination to help advance the interaction between the predominately oil-soluble surfactant and the predominately water-soluble surfactant as well as the co-solvent. The water component also helps reduce the viscosity of the dispersant to allow it to be pumped under pressure.

U.S. Pat. No. 6,194,473, to Lessard et al., describes a formulation of chemical surfactants, solvents and inorganic salts which is effective for dispersing heavy oils in both salt and fresh water. The formulation comprises a mixture of a sorbitan ester of an aliphatic monocarboxylic acid, a polyoxyethylene adduct of a sorbitan monoester of an aliphatic monocarboxylic acid, an alkali metal salt of a dialkyl sulfosuccinate, a polyoxyethylene adduct of a sorbitan triester of a monocarboxylic acid, a solvent comprising a hydrocarbon and/or a glycol ether and an inorganic salt containing a soluble divalent cation such as calcium or magnesium.

U.S. Pat. No. 5,454,978, to Vanderpool et al, describes a surface active composition for dispersing an oil in an aqueous media and/or for inhibiting deposition of oil on a surface of a water carrying system. Preferably, the water carrying system is at least one system selected from the group consisting of a cooling tower, a cooling tower fill, means for heat exchange, means for industrial processing, and a body of water. A method for inhibiting deposition of an oil on a surface of a water carrying system is also provided.

U.S. Pat. No. 5,422,011, to Avila, teaches a method for recuperating crude oil from the body of a spill. First, the body of the spill is sprayed at low pressure then the same operation is done at a relatively higher pressure of at least 100 p.s.i. After the dispersant is allowed to penetrate the body of the spill for several hours, physical agitation of the body of the spill is induced by the use of air compressors operating in the range between 500 and 700 psi causing the crude oil to disperse and come to the surface. The crude oil is then extracted from the spill through the use of skimmers and vacuum suction means and subsequently processed.

U.S. Pat. No. 5,302,320, to Hosmer et al describes an emulsification agent for hydrocarbons comprising an ethoxylated nonylphenol, the reaction product of tall oil and an alkanolamine and tripropylene glycol methyl ether. The agent optionally can include sodium xylene sulfonate.

U.S. Pat. No. 4,992,213, to Mallett et al., relates to a composition which is designed to be used as a cleaning agent and oil dispersant. The composition has a number of active ingredients mixed with water. The solution provides for the use of such active ingredients as sodium lauryl sulfate, cocamidopropyl betaine, ethoxylated nonylphenol, lauric acid diethanolamide, diethanolamine and propylene glycol. Preferred compositions contain the following ingredients mixed in an aqueous base: from 0.02% to 2.25% by total weight of sodium lauryl sulfate, from 0.02% to 1.95% by total weight of cocamidopropyl betaine, from 0.002% to 0.25% by total weight of ethoxylated nonylphenol, from 0.04% to 4.25% of lauric acid diethanolamide, from 0.02% to 1.85% by total weight of diethanolamine and from 0.02% to 1.85% by total weight of propylene glycol.

U.S. Pat. No. 4,948,531, to Fuggini et al., describes compositions for cleaning hard surfaces, which are formulated to leave on the surface simultaneously with the cleaning thereof a protective barrier layer which serves to protect the surface against further soil deposition, comprising: (A), as cleaning agents, from one to two nonionic surfactants and an amphoteric surfactant (B), as protective barrier components, lecithin and an aminofunctional polydimethylsiloxane copolymer; (C), as solvency and grease cutting agents, from one to two glycols; and (D) water.

U.S. Pat. No. 4,764,285, to Robbins et al., discloses a method for dispersing an oil spill on sea water which method comprises applying to the oil spill surface an effective amount of: (i) a blend of one or more hydrophilic and one or more lipophilic surfactants whose ratio is so adjusted that they will form microemulsions with the sea water and the oil to be dispersed, (ii) a solvent which is miscible with the oil to be dispersed and in which the blend of surfactants is substantially soluble, and (iii) from 0 to about 10 wt. % water. The blend of surfactants is such that it lowers the interfacial tension between the oil to be dispersed and the sea water to less than about 250 mdynes/cm when the blend is used at a treating rate of less than about 1 to 100 by weight, based on the weight of the oil to be dispersed.

U.S. Pat. No. 4,502,962, to Becker et al., teaches a hydrocarbon solvent-based dispersant formulation which combines heavy oil penetrability, activity on oil spills on either fresh or salt water, and the density and viscosity required for controllable aerial spray application is provided by the combination of sorbitan monoesters of $C_{10}$-$C_{20}$ aliphatic carboxylic acids and polyoxyalkylene adducts thereof, polyoxyalkylene adducts of sorbitan triesters of $C_{10}$-$C_{20}$ aliphatic carboxylic acids, and a water-dispersible salt of a dialkyl sulfosuccinate dissolved in an isoparaffinic hydrocarbon. The addition of a viscosity modifying solvent may be advantageous for adjusting the formulation to needs of specific aerial application procedure.

U.S. Pat. No. 3,996,134, to Osborn et al., is directed toward a method of dispersing oil in water, particularly useful in oil slick dispersion, secondary oil recovery and tar-sand oil recovery, which comprises contacting the oil and water with an alkyd resin in which one component of the resin is the residue of a water-soluble polyalkylene glycol such as a polyethylene glycol.

U.S. Pat. No. 3,960,742, to Leonard, is directed toward a solvent emulsion type cleaner concentrate, which provides effective cleaning at recommended water dilutions of 896:1. The concentrate comprises about 30-60 parts by weight of an ethylene glycol monoalkyl ether solvent, together with inorganic alkaline solids and small amounts of two or more solids-suspending surfactants. The concentrate is non-flammable, ecologically acceptable, relatively non-toxic, and has corrosion inhibiting properties.

U.S. Pat. No. 3,948,770, to Goodrich et al., teaches that mixtures of finely dispersed oil droplets in sea water which are often present in oil tanker compartments may be effectively separated by a chemical flocculating agent comprising a dry powdered mixture of an anionic polyelectrolyte and a sodium or calcium montmorillonite clay.

U.S. Pat. No. 3,577,340, to Paviak et al., teaches a method for dissipating oil spills floating on a body of water by dispersing the spilled oil with a novel alkylphenol ethoxylate.

U.S. Pat. No. 3,457,168, to Malmberg et al., teaches a method of dispersing a petroleum oil layer from the surface of a body of open water comprising coating the exposed surface of the oil with a layer of foamed surfactant and subsequently vigorously agitating the water-oil-surfactant layers after the foamed surfactant has become substantially digested by the oil layer.

US Published Application 2011/0257015, to Bergeron et al., relates to a polymeric material comprising units capable of having a cationic charge at a pH of from about 4 to about 12; provided that said polymeric material has an average cationic charge density from about 2.75 or less units per 100 daltons molecular weight at a pH of from about 4 to about 12. The polymeric material is a suds enhancer and a suds volume extender for hand dishwashing compositions and personal care products such as soaps, shaving cream foam, foaming shaving gel, foam depilatories and shampoos. The polymers are also effective as a soil release agent in fabric cleaning compositions. The polymers are also useful in agrochemical foam, fire-fighting foam, hard surface cleaner foam, and coagulant for titanium dioxide in papermaking.

International Application WO 05097130A1, to Gilbard et al, is directed to novel compositions and methods effective for maintaining eyelid hygiene, e.g., therapeutic treatment and prophylaxis. The present invention further provides cleanser compositions and methods that are compliance enhancing and useful for daily prophylaxis involving the easy and safe application directly to the eyelid in controlled doses for maintenance of eyelid hygiene. The cleanser compositions of the present invention can be in the form of a foam.

The prior art cited herein fails to teach or suggest an oil dispersant composition inclusive of the particular blend of ingredients disclosed herein. Likewise, the prior art fails to teach or suggest the method of providing hydrocarbon and lipid degradation in order to enhance the remediation of the affected areas.

SUMMARY OF THE INVENTION

The present invention is directed toward a novel composition useful in treating oil spills, e.g. as an oil dispersant, and for cleanup of the shoreline, animals, plants, and equipment. The composition is also useful for the treatment of build-up of fats, oils and grease (FOG), in soil, bodies of water, pipelines, and the like. In an embodiment, the composition is further useful for the remediation of soils, bodies of water, contaminated facilities, e.g. buildings and the like, in order to both disperse hydrocarbon and/or lipid contaminants, while fully digesting any residual materials in order to fully remediate such areas. Various embodiments are contemplated as being useful for soil remediation, e.g. for soil and equipment clean up; and in the automotive industry as a degreaser and oil release agent, and in auto repair shops. Additional utilities can be found in the oil transport, aerospace, e.g. aircraft fuselage and engine cleanup, food preparation industries, hazardous waste treatment, and the like.

In an embodiment, the oil dispersant composition is supplied as a homogeneous mixture prepared by mixing, in sequence, the following ingredients:
1) 7.3%-9.3% by weight of cocoamidopropyl-betaine;
2) 6.8%-8.3% by weight of tall oil fatty acid;
3) 7.9%-9.7% by weight monoethanolamine;
4) 7.9%-9.7% by weight of a Nonionic Octylphenol Ethoxylate having the formula:

$$R\!-\!\!\left\langle\!\!\bigcirc\!\!\right\rangle\!\!-\!\!O\!\!\left[\!\!-\!\!CH_2CH_2\!-\!\!O\!\right]_x\!\!H$$

wherein R=octyl ($C_8$) and x=4.5 (avg);
5) 8.3%-10.4% by weight of a Nonionic Octylphenol Ethoxylate having the formula:

$$R\!-\!\!\left\langle\!\!\bigcirc\!\!\right\rangle\!\!-\!\!O\!\!\left[\!\!-\!\!CH_2CH_2\!-\!\!O\!\right]_x\!\!H$$

wherein R=octyl ($C_8$) and x=9.5 (avg);
6) 8.4%-10.5% by weight of the tetrasodium salt of ethylenediaminetetraacetic acid; and
7) water to make 100% by weight.

In another embodiment, the oil dispersant composition is supplied as a homogeneous mixture of the following ingredients, blended in sequence, for a time sufficient to provide a uniformly blended intermediate prior to addition of the next ingredient:
1) 8.87% by weight of cocoamidopropyl-betaine;
2) 7.74% by weight of tall oil fatty acid;
3) 8.68% by weight monoethanolamine;
4) 8.87% by weight of a Nonionic Octylphenol Ethoxylate having the formula:

$$R\!-\!\!\left\langle\!\!\bigcirc\!\!\right\rangle\!\!-\!\!O\!\!\left[\!\!-\!\!CH_2CH_2\!-\!\!O\!\right]_x\!\!H$$

wherein R=octyl ($C_8$) and x=4.5 (avg);
5) 9.06% by weight of a Nonionic Octylphenol Ethoxylate having the formula:

$$R\!-\!\!\left\langle\!\!\bigcirc\!\!\right\rangle\!\!-\!\!O\!\!\left[\!\!-\!\!CH_2CH_2\!-\!\!O\!\right]_x\!\!H$$

wherein R=octyl ($C_8$) and x=9.5 (avg);
6) 9.15% by weight of the tetrasodium salt of ethylenediaminetetraacetic acid; and
7) 47.63% by weight water.

In another embodiment, it is within the purview of the present invention to substitute the nonionic octylphenol ethoxylates ingredients with equivalent amounts of an alternative sugar such as Ficoll, Sucrose, Fructose, Glycine, Glycerol, or the like, and combinations thereof.

To any of the illustrated embodiments it is within the purview of the instant invention to add one or more biological hydrocarbon degraders.

In accordance with the present invention, biological hydrocarbon degraders are defined as aerobic and/or anaerobic microorganisms selected from the families *Bacillus, Pseudomonas, Paenibacillus* and *Aspergillus*. The microorganisms are selected on the basis of their suitability for degrading such materials as benzene, toluene, and xylene (BTEX), petroleum hydrocarbon fractions F1-F4 (as defined by CCME2000), and polycyclic aromatic hydrocarbons. It is within the purview of the present invention to utilize environmentally modified, transitioned or evolved microorganisms for optimal hydrocarbon degradation in combination with the disclosed DXR™ oil dispersant formulation in order to maximize the efficiency of treatment.

Such microorganisms are useful, in combination with any of the oil dispersant embodiments illustrated herein, of remediating soil, treating oil-water separators, catch basins, and the like.

In combination with certain strains of bacilli, the dispersants are particularly advantageous in treating fat, oil and grease build-up (FOG). Tests have also demonstrated their utility in degrading the build-up of paraffin waxes, mold removal and reduction of volatile organic contaminants.

The resultant composition is a novel blend of microorganisms, cleansers and surfactants which is non-toxic and solvent free, and which has the ability to accelerate the breaking down process of oils, materials such as benzene, toluene, and xylene (BTEX); petroleum hydrocarbon fractions F1-F4 (as defined by CCME2000), polycyclic aromatic hydrocarbons (PAH), paraffin waxes, volatile organics, molds, and the like; while simultaneously providing a biological component which is effective to reduce the total petroleum hydrocarbon levels to zero at an accelerated rate.

Accordingly, it is a primary objective of the instant invention to teach a novel composition for use as both a solvent-free oil dispersant and bioremediation composition.

It is a further objective of the instant invention to teach a method of manufacture of the instantly disclosed composition.

It is yet another objective of the instant invention to teach an oil dispersant and bioremediation composition that eliminates the toxicity issues attributable to solvent based, heavy metal containing, toxic oil dispersants, which are currently the product of choice for major oil, spill treatment procedures.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

The invention is directed toward a novel composition comprised of the combination of an oil dispersant composition and a biological hydrocarbon degrader, and methods for their production and use.

In its broadest context, the invention is a composition of matter including a novel oil dispersant/surfactant composition, which contains a number of ingredients, which are formulated in a particular sequence in order to arrive at the novel oil dispersant as herein disclosed and claimed; in combination with at least one biological hydrocarbon degrader selected from aerobic and/or anaerobic microorganisms of the families *Bacillus, Pseudomonas, Paenibacillus* and *Aspergillus*, as well as environmentally modified, transitioned or evolved strains thereof, in an amount effective for optimal hydrocarbon degradation.

The broadly disclosed composition is formulated by providing the following ingredients within the ranges stated:

1) 7.3%-9.3% by weight of cocoamidopropyl-betaine;
2) 6.8%-8.3% by weight of tall oil fatty acid;
3) 7.9%-9.7% by weight monoethanolamine;
4) 7.9%-9.7% by weight of a Nonionic Octylphenol Ethoxylate having the formula:

wherein R=octyl ($C_8$) and x=4.5 (avg);

5) 8.3%-10.4% by weight of a Nonionic Octylphenol Ethoxylate having the formula:

wherein R=octyl ($C_8$) and x=9.5 (avg);

6) 8.4%-10.5% by weight of the tetrasodium salt of ethylenediaminetetraacetic acid; and

7) water to make 100% by weight.

Cocamidopropyl betaine (CAPB) is a synthetic surfactant derived from coconut oil and dimethylaminopropylamine. It is a zwitterionic chemical compound with a quaternary ammonium cation. It is a viscous pale yellow transparent liquid and is used as a surfactant in bath products such as shampoos and hand soaps, and in cosmetics as an emulsifying agent and thickener, and to reduce irritation purely ionic surfactants would cause. It also serves as an antistatic agent in hair conditioners. CAPB is available from Spectrum Laboratories in Gardena, Calif.

Tall oil fatty acid is available under the brand name SYLFAT® FA2, from Arizona Chemical Company of Jacksonville, Fla. The material is an intermediate in the manufacture of soaps, dimer acids, amines, amides, imidazolines, alkyd resins, coatings, and polyesters. It is useful in areas such as specialty industrial and household cleaners, plasticizers for rubber products, textiles, and surfactants.

Monoethanolamine, MEA, is an absorbent chemical employed, for example, in carbon dioxide scrubbers aboard nuclear submarines. It is available from the Sciencelab Company in Houston, Tex.

A Nonionic Octylphenol Ethoxylate surfactant composition having the formula:

R = octyl (C8)
x = 4.5 (avg)

is available as Triton™ X-45 from Dow Chemical Company. It is useful in defoamers, cleaners, metalworking fluids, agrochemicals, textiles, pulp and paper manufacture, oilfields, paints and coatings.

A Nonionic Octyiphenol Ethoxylate surfactant composition having the formula:

R = Octyl (C8)
x = 9.5 (avg)

is available as Triton™ X-100 from the Dow Chemical Company. It is useful in Household and Industrial cleaners, metalworking fluids, agrochemicals, textiles, pulp and paper manufacture, oilfields, paints and coatings.

The tetrasodium salt of ethylenediaminetetraacetic acid is available as VERSENE™ 100, from the Dow Chemical Company. VERSENE™ 100 is described as a chelating agent, provided as an aqueous solution of the tetrasodium salt of ethylenediaminetetraacetic acid. ($Na_4EDTA$). It will chelate most multivalent metal ions (e.g., Fe, Cu, Mn, Ca, Mg, Zn) in a 1:1 molar ratio. VERSENE™ 100 is completely miscible with water, but is not soluble in organic systems. $Na_4EDTA$ is stable under widely varying conditions of temperature, acidity, alkalinity, and the presence of other chemicals. Applications include agriculture, cleaning products, metalworking, oilfield applications, personal care products, polymerization, pulp and paper, scale removal and prevention, textiles, water treatment.

In a method of manufacture, the ingredients are added sequentially to a vessel, e.g. a high-density polyethylene beaker, and blended with a mixer, e.g. a Lightnin Mixer, available from the SPX Corporation in Rochester, N.Y. Each ingredient is added in sequential order, and mixing is conducted in a stepwise fashion for about 10 minutes per ingredient, or until a uniform blend is produced, before addition of the next ingredient. While in the mixing stage, some heat is produced, typically reaching a temperature of about 45° C. Upon cooling, the resultant product is a clear liquid having a slightly yellowish color. It is understood that as the batch size increases, the skilled artisan will extend the mixing time between steps so as to assure uniform blending.

In another method of manufacture, the composition, designated DXR-02™, is an oil dispersant supplied as a homogeneous mixture of the following ingredients, blended in sequence, for a time sufficient to provide a uniformly blended intermediate prior to addition of the next ingredient:
1) 8.87% by weight of cocoamidopropyl-betaine;
2) 7.74% by weight of tall oil fatty acid;
3) 8.68% by weight monoethanolamine;
4) 8.87% by weight of a Nonionic Octylphenol Ethoxylate having the formula:

wherein R=octyl ($C_8$) and x=4.5 (avg);
5) 9.06% by weight of a Nonionic Octylphenol Ethoxylate having the formula:

wherein R=octyl ($C_8$) and x=9.5 (avg);
6) 9.15% by weight of the tetrasodium salt of ethylenediaminetetraacetic acid; and
7) 47.63% by weight water.

The composition further includes at least one biological hydrocarbon degrader selected from aerobic and/or anaerobic microorganisms of the families *Bacillus, Pseudomonas, Paenibacillus* and *Aspergillus*, as well as environmentally modified, transitioned or evolved strains thereof in an amount effective for optimal hydrocarbon degradation.

In a further embodiment, it is within the purview of the present invention to substitute the nonionic octylphenol ethoxylates with equivalent amounts of an alternative sugar such as Ficoll, Sucrose, Fructose, Glycine, Glycerol, or the like, and combinations thereof.

Figure 1:
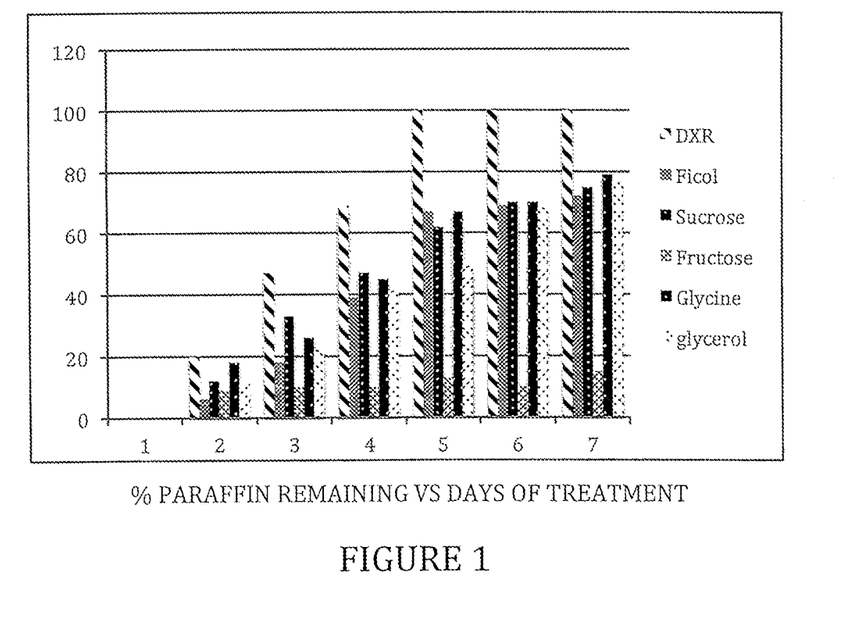
FIG. 1 illustrates relative effectiveness of DXR versus modified surfactant formulations substituting alternative sugars for breakdown of paraffin.

As illustrated in FIG. 1, formulations were prepared using Ficoll, Sucrose, Fructose, Glycine, and Glycerol in place of the Nonionic Octylphenol Ethoxylates. Tests were carried out to determine the percentage of paraffin wax (y-axis) versus the days of treatment (x-axis) in order to develop a comparison of effectiveness. While various of the sugar substitutions yielded compositions effective as paraffin dispersants, the DXR formulation was still superior in this regard.

It has been the inventor's experience that when formulating larger batches, e.g. 1000 KG, the mixing times increase to about 30 minutes per sequence in order to assure uniformity.

A study was conducted to assess the toxicity of the test substance, DXR-02™, to Mysidopsis Bahia, in a 96-hour static, non-renewal test.

Test concentrations were determined by a preliminary range-finding test. A definitive test was conducted using concentrations of 50, 100, 200, 400 and 800 mg/L of the test substance. Each test concentration consisted of three replicates often organisms (greater amount than the protocol requirement of 20 organisms). Organisms were randomly placed, individually, into each test container containing the appropriate concentration of test substance. Three replicates often (10) organisms were not exposed to test substance and served as controls to demonstrate the condition of the test population. At 0, 24, 48, 72 and 96 hours following dosing, each test container was examined for mortality, and the number of live shrimp was recorded. The test was terminated after 96±1 hours of exposure.

The 96-hour median effective concentration (EC50) of DXR-02™ was determined to be 475.00 mg/L with 95% confidence limits of 0.00-677.50 mg/L. The NOEC (No Observed Effect Concentration) for survival was determined to be 100 mg/L. Results presented are based on nominal concentrations.

Comparisons of 48 hour toxicity with respect to various commercial products are illustrated in Table 1:

TABLE 1

| Toxicity Comparison | | | | | |
|---|---|---|---|---|---|
| Material Tested | Species | LC50 (ppm) | TIME | LD50 Death | Test guide lines |
| DXR-02 ™ | *Mysidopsis bahia* | 600 | 48 hr | | OCSPP 850.1035 |
| BIODISPERS | *Mysidopsis bahia* | 78.9 | 48 hr | N/A | |
| COREX EC9500A | *Mysidopsis bahia* | 32.23 | 48 hr | N/A | |
| COREXIT EC9527A | *Mysidopsis bahia* | 24.14 | 48 hr | N/A | |
| FINASOL OSR 52 | *Mysidopsis bahia* | 9.37 | 48 hr | N/A | |

As evidenced by the values set forth in Table 1, the LC50 in PPM of DXR-02™ is between about 8 and 20 times that of the commercially available oil dispersants tested.

The presences of toxic materials such as heavy metal was evaluated with respect to alternative, commercially available oil dispersants and are reported in Table 2.

TABLE 2

| Product | Arsenic | Cadmium | Chromium | Copper | Lead | Mercury | Nickel | Zinc | Cyanide |
|---|---|---|---|---|---|---|---|---|---|
| DXR-02 ™ | 0 | 0 | 0 | 0 | 0 | 0 | 0 | 0 | 0 |
| BIODISPERS | <2.5 | <0.75 | <0.75 | <0.5 | <5.0 | N/D | <1.20 | <0.50 | 3.9 |
| COREXIT EC9500A | 0.16 | N/D | 0.03 | 0.1 | N/D | N/D | N/D | N/D | N/D |
| COREXIT EC9527A | <0.005 | <0.01 | <1.0 | <0.2 | <0.1 | <0.003 | <0.1 | 0.1 | <0.01 |
| FINASOL OSR 52 | <10.0 | <10.0 | <10.0 | <10.0 | <10.0 | <1 | <10.0 | <10.0 | <0.4 |
| JD-109 | <10.0 | <10.0 | <10.0 | <10.0 | <1 | <10.0 | <10.0 | <10.0 | <0.5 |
| JD-2000 | <0.24 | <10.0 | <10.0 | <10.0 | <0.43 | <10.0 | <10.0 | <0.11 | <0.20 |
| MARE CLEAN 200 | <0.50 | <0.10 | <0.50 | <0.250 | <2.5 | <0.0200 | <2.5 | 0.611 | <0.01 |
| NEOS AB3000 | <0.1 | <0.1 | 0.26 | <0.05 | 0.21 | <0.001 | 0.076 | 1.1 | <0.05 |

Table 2 illustrates that DXR-02™ is the only oil dispersant tested which did not contain heavy metals. This is thought to be due to the absence of any solvents in the production of the DXR-02™ oil dispersant of the present invention.

The dispersant properties of the composition of the invention were determined in accordance with ASTM-F2059, Laboratory Oil Spill Dispersant Effectiveness Using the Swirling Flask. The % Effectiveness is illustrated in Table 3.

TABLE 3

Material Tested - South Louisiana Crude

| Oil Dispersant | % Effectiveness |
|---|---|
| DXR-02 ™ | 74.28% |
| BIODISPERS | 63% |
| COREX EC9500A | 54.70% |
| COREXIT EC9527A | 63.4 |
| FINASOL OSR 52 | 71.60% |

This test establishes a baseline performance parameter so that dispersants can be compared, a given dispersant can be compared for effectiveness on different oils, and at different oil weathering stages, and batches of dispersant or oils can be checked for effectiveness changes with time or other factors. Basically, the test method covers the procedure to determine the effectiveness of oil spill dispersants on various oils in the laboratory. This test method covers the use of the swirling flask test apparatus. Results obtained using this test method are intended to provide baseline effectiveness values used to compare dispersants and oil types under conditions analogous to those used in the test.

Acute Oral Toxicity in Rats

The test material, DXR-02™, was tested in rats to assess an Acute Oral Toxicity. The test yielded the following result:

In a Limit Screen, an oral 5000 mg/kg (body weight) dose of this test material, when administered to five female Sprague-Dawley rats, did not result in any mortality or abnormalities. The LD50 is thus greater than 5000 mg/kg. According to the Guide to the Globally Harmonized System for Classification and Labeling of Chemicals (GHS), the classification of chemicals, as well as Acute Oral Toxicity LD50 (mg/kg) for EPA/US/FIFRA, are classified as follows:

| $LD_{50}$ (mg/kg) | Toxic Category | Acute Toxicity Definition |
|---|---|---|
| 0 ≤ 50 | Toxicity Category I | High |
| >50 ≤ 500 | Toxicity Category II | Hazard |
| >500 < 5000 | Toxic Category III | Hazard |
| >5000 | Toxic Category IV | Low |

The $LD_{50}$ for DXR-02™ was determined to be greater than 5000 mg/kg, which according to above categories, the acute toxicity of this product is low.

Figure 2:
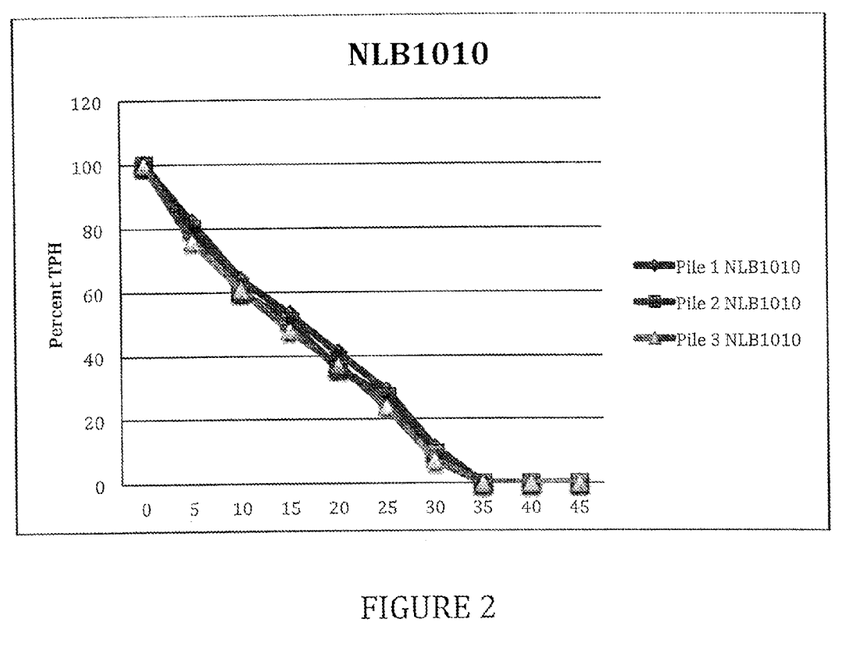
FIG. 2 illustrates use of a 1:1 blend of DXR and NLB1000 to treat hydrocarbon contamination in soil.

Now referring to FIG. 2, a field test of DXR™ was conducted using DXR in a 1:1 ratio with a cocktail of microbes obtained from New Leaf Biologics Inc. in Manitoba, Canada, designated NLB1000. NLB1000 is a cocktail of microbes used for hydrocarbon degradation. While the 1:1 ratio represents an effective embodiment for hydrocarbon degradation, it is understood that this is a non-limiting embodiment, and that various other effective ratios are within the purview of the present invention, so long as they are effective for A 3 cubic foot sample of soil spiked with petroleum hydrocarbons was provided. The test was run in triplicate. To Piles 1, 2 and 3 the 1:1 combination of DXR and NLB1000 was added by spraying onto the piles. As can be seen in FIG. 2, the percentage of total petroleum hydrocarbons (TPH) was fully degraded by about day 30.

Although the field test was conducted with NLB1000, in accordance with the present invention, suitable biological hydrocarbon degraders include, but are not limited to, aerobic and/or anaerobic microorganisms selected from the families *Bacillus, Pseudomonas, Paenibacillus* and *Aspergillus*, as well as environmentally modified, transitioned or evolved strains thereof for optimal hydrocarbon degradation in combination with the disclosed DXR™ oil dispersant formulation in order to maximize the efficiency of treatment. The microorganisms are selected on the basis of their suitability for degrading such materials as benzene, toluene, and xylene (BTEX), petroleum hydrocarbon fractions F1-F4 (as defined by CCME2000), and polycyclic aromatic hydrocarbons.

Figure 3:
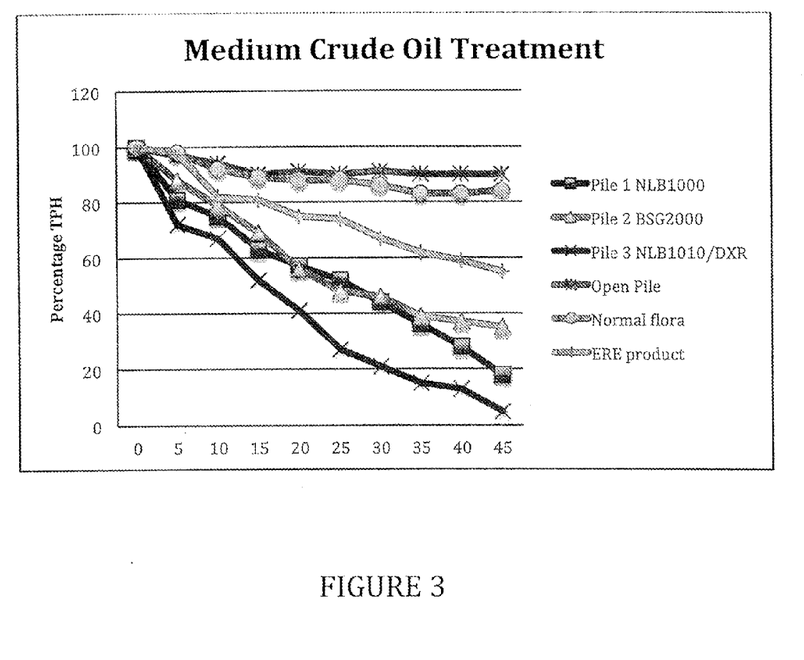
FIG. 3 illustrates the use of the product of the present invention in a comparative analysis demonstrating the treatment of medium crude oil contamination in soil.

Now referring to FIG. 3, the NLB1000/DXR 1:1 blend (designated NLB1010) was tested to compare different hydrocarbon degrading products on a medium crude oil contaminated test pile. The piles were dosed as follows:

Pile 1—NLB1000; Pile 2—BSG2000 (Biosolv Green 2000); Pile 3—NLB1010; Pile 4—Open Pile—Autoclaved to kill off any microbes; Pile 5—Normal flora—an open pile containing indigenous flora; Pile 6—dosed with ERE microbe blend (a competitive microbial composition).

As can be seen from the graph of FIG. 3, the percentage of Total Petroleum Hydrocarbons provided by the medium crude oil contaminant was degraded at various rates. After 45 days, only the NLB1010 sample was virtually devoid of petroleum hydrocarbon contamination, showing the superiority of the instantly disclosed invention for remediating petroleum hydrocarbon contamination in soils.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention, which are obvious to those skilled in the art, are intended to be within the scope of the following claims.

What is claimed is:

1. A composition useful as a petroleum hydrocarbon dispersant and remediation composition comprising in combination:
   1) 7.3%-9.3% by weight of cocoamidopropyl-betaine;
   2) 6.8%-8.3% by weight of tall oil fatty acid;
   3) 7.9%-9.7% by weight monoethanolamine;
   4) 7.9%-9.7% by weight of a Nonionic Octylphenol Ethoxylate having the formula:

wherein R=octyl ($C_8$) and x=4.5 (avg);
   5) 8.3%-10.4% by weight of a Nonionic Octylphenol Ethoxylate having the formula:

wherein R=octyl ($C_8$) and x=9.5 (avg);
   6) 8.4%-10.5% by weight of a tetrasodium salt of ethylenediaminetetraacetic acid;
   (7) at least one biological hydrocarbon degrader selected from aerobic and/or anaerobic microorganisms of the families *Bacillus, Pseudomonas, Paenibacillus* and *Aspergillus*, as well as environmentally modified, transitioned or evolved strains thereof in an amount effective for optimal hydrocarbon degradation; and
   8) water to make 100% by weight.

2. The composition of claim 1 comprising:
   1) 8.87% by weight of cocoamidopropyl-betaine;
   2) 7.74% by weight of tall oil fatty acid;
   3) 8.68% by weight monoethanolamine;
   4) 8.87% by weight of a Nonionic Octylphenol Ethoxylate having the formula:

wherein R=octyl ($C_8$) and x=4.5 (avg);
   5) 9.06% by weight of a Nonionic Octylphenol Ethoxylate having the formula:

wherein R=octyl ($C_8$) and x=9.5 (avg);
   6) 9.15% by weight of a tetrasodium salt of ethylenediaminetetraacetic acid; and
   7) 47.63% by weight water.

3. A process for the treatment of oil spills, soil remediation, degreasing and release of oil in the automotive industry, and oil dispersal and equipment clean-up in the oil transport, aerospace and food preparation industries comprising:
   providing a composition which includes 7.3%-9.3% by weight of cocoamidopropyl-betaine; 6.8%-8.3% by weight of tall oil fatty acid; 7.9%-9.7% by weight monoethanolamine; 7.9%-9.7% by weight of a Nonionic Octylphenol Ethoxylate having the formula:

wherein R=octyl ($C_8$) and x=4.5 (avg); 8.3%-10.4% by weight of a Nonionic Octylphenol Ethoxylate having the formula:

wherein R=octyl ($C_8$) and x=9.5 (avg); 8.4%-10.5% by weight of a tetrasodium salt of ethylenediaminetetraacetic acid;
   providing at least one biological hydrocarbon degrader selected from aerobic and/or anaerobic microorganisms of the families *Bacillus, Pseudomonas, Paenibacillus* and *Aspergillus*, as well as environmentally modified, transitioned or evolved strains thereof in an amount effective for optimal hydrocarbon degradation;
   providing water to make 100% by weight; and
   contacting an oil spill, soil in need of remediation, fats, oils and grease (FOG), automotive components requiring degreasing or release of oil, and equipment in need of clean-up from the oil transport, aerospace and food preparation industries with said composition;
   whereby oil spill treatment, soil remediation, degreasing and release of oil in the automotive industry, and oil dispersal and equipment clean-up in the oil transport, aerospace and food preparation industries are effected.

4. A process for the treatment of oil spills, soil remediation, degreasing and release of oil in the automotive industry, and oil dispersal and equipment clean-up in the oil transport, aerospace and food preparation industries comprising:

providing a composition which includes 8.87% by weight of cocoamidopropyl-betaine; 7.74% by weight of tall oil fatty acid; 8.68% by weight monoethanolamine; 8.87% by weight of a Nonionic Octylphenol Ethoxylate having the formula:

wherein R=octyl ($C_8$) and x=4.5 (avg); 9.06% by weight of a Nonionic Octylphenol Ethoxylate having the formula:

wherein R=octyl ($C_8$) and x=9.5 (avg); 9.15% by weight of a tetrasodium salt of ethylenediaminetetraacetic acid; and 47.63% by weight water; and providing at least one biological hydrocarbon degrader selected from aerobic and/or anaerobic microorganisms of the families *Bacillus, Pseudomonas, Paenibacillus* and *Aspergillus*, as well as environmentally modified, transitioned or evolved strains thereof in an amount effective for optimal hydrocarbon degradation; and contacting an oil spill, soil in need of remediation, fats, oils and grease (FOG), automotive components requiring degreasing or release of oil, and equipment in need of clean-up from the oil transport, aerospace and food preparation industries with said composition;

whereby oil spill treatment, soil remediation, degreasing and release of oil in the automotive industry, and oil dispersal and equipment clean-up in the oil transport, aerospace and food preparation industries are effected.

5. The composition of claim 1, wherein the nonionic octylphenol ethoxylates are replaced with like amounts of at least one alternative sugar selected from the group consisting of a Ficoll, a Sucrose, a Fructose, a Glycine, and a Glycerol.

6. The process of claim 3, wherein the nonionic octylphenol ethoxylates are replaced with like amounts of at least one alternative sugar selected from the group consisting of a Ficoll, a Sucrose, a Fructose, a Glycine, and a Glycerol.

* * * * *